(12) United States Patent
Taya et al.

(10) Patent No.: US 9,140,654 B2
(45) Date of Patent: Sep. 22, 2015

(54) INSPECTION APPARATUS

(71) Applicant: NUFLARE TECHNOLOGY, INC., Kanagawa (JP)

(72) Inventors: Makoto Taya, Tokyo (JP); Nobutaka Kikuiri, Tokyo (JP)

(73) Assignee: NUFLARE TECHNOLOGY, INC., Kanagawa (JP)

( * ) Notice: Subject to any disclaimer, the term of this patent is extended or adjusted under 35 U.S.C. 154(b) by 0 days.

(21) Appl. No.: 14/259,008

(22) Filed: Apr. 22, 2014

(65) Prior Publication Data

US 2014/0320860 A1    Oct. 30, 2014

(30) Foreign Application Priority Data

Apr. 26, 2013    (JP) .................................. 2013-094044

(51) Int. Cl.
*G01N 21/00*    (2006.01)
*G01N 21/956*    (2006.01)

(52) U.S. Cl.
CPC ........ *G01N 21/95607* (2013.01); *G01N 21/956* (2013.01)

(58) Field of Classification Search
CPC .......... G01N 21/95607; G01N 21/956; G01N 21/9501
USPC ............................................. 356/237.1–237.5
See application file for complete search history.

(56) References Cited

U.S. PATENT DOCUMENTS

| 2003/0099035 A1* | 5/2003 | Kawarabata et al. | 359/385 |
| 2005/0052642 A1* | 3/2005 | Shibata et al. | 356/237.1 |
| 2005/0264802 A1* | 12/2005 | Shibata et al. | 356/237.5 |

FOREIGN PATENT DOCUMENTS

| JP | 09-082599 | 3/1997 |
| JP | 09-134865 | 5/1997 |
| JP | 2007-248086 | 9/2007 |
| JP | 2008-112178 | 5/2008 |

* cited by examiner

*Primary Examiner* — Hoa Pham
(74) *Attorney, Agent, or Firm* — Patterson & Sheridan LLP

(57) ABSTRACT

An inspection apparatus comprising, a light source configured to emit an inspection light, a table configured to mount an inspection target thereon, an illumination optical system configured to direct the inspection light from the light source toward the target, an objective lens unit configured to gather transmitting or reflected light generated after the illumination optical system illuminates the target with the inspection light, a light receiving unit configured to capture an optical image formed from the light illuminated through the objective lens unit, a chamber configured to house the table, light receiving unit, illumination optical system and objective lens unit, a temperature adjustment unit configured to adjust a temperature in the chamber, and a gas supply unit configured to be connected to the objective lens unit to supply an inert gas at a predetermined temperature into the unit.

9 Claims, 8 Drawing Sheets

INSPECTION APPARATUS

CROSS-REFERENCE TO THE RELATED APPLICATION

The entire disclosure of the Japanese Patent Application No. 2013-094044, filed on Apr. 26, 2013 including specification, claims, drawings, and summary, on which the Convention priority of the present application is based, are incorporated herein in its entirety.

FIELD OF THE INVENTION

The present invention relates to an Inspection Apparatus. With high integration and large capacity of a Large Scale Integration (LSI), a circuit dimension required for a semiconductor element becomes increasingly narrowed. For example, a pattern having a line width of several tens of nanometers is required to be formed in the latest typical logic device.

It is necessary to improve a production yield of the expensive LSI in a production process. In the semiconductor element, during a production process, an original graphic pattern (that is, a mask or a reticle, hereinafter collectively referred to as a mask) in which a circuit pattern is formed is exposed and transferred onto a wafer by a reduction projection exposure apparatus called a stepper or a scanner. A shape defect of a mask pattern and fluctuations of various process conditions while the pattern is exposed and transferred, can be cited as a large factor that reduces a production yield of the semiconductor element.

The finer the dimensions of an LSI pattern formed on the wafer becomes, the finer the shape defect of the mask pattern becomes. As fluctuations of various process conditions are absorbed by enhancing dimensional accuracy of the mask, it is necessary to defect the defect of the extremely small pattern in a mask inspection. Therefore, high accuracy is required for an apparatus that inspects the pattern of a transfer mask used in the LSI production.

In the inspection apparatus, light output from the light source is emitted onto the mask, which is an inspection target through an illumination optical system. The mask is mounted on the table, and the emitted light scans the mask while the table moves. The light transmits or is reflected with respect to the mask, and passes through the objective lens to form an optical image on an image sensor, which serves as a light receiving unit. Then, the optical image is captured by the image sensor, and sent to a comparing unit as measurement data. The comparing unit compares the measurement data and reference data according to an appropriate algorithm. Then, in a case where the data does not match with each other, it is determined that there is a defect (see, for example, JP 2008-112178 A and JP 2007-248086 A).

In recent years, an inspection apparatus needs to detect a defect in very small patterns to deal with microfabrication of patterns formed on the mask. Therefore, an inspection optical system which includes a light source, an illumination optical system, an objective lens, an image sensor, and the like to capture an optical image of the pattern, is in an advanced stage of high magnification and high NA (Numerical Aperture). As a result, the objective lens is necessarily expanded in magnification and the depth of focus therefore becomes shallow.

Incidentally, in the inspection apparatus, relative refractive indexes of the respective lenses constituting the objective lens vary depending on a change in temperature or atmosphere pressure of the surrounding area of the apparatus. Further, holders for holding the respective lenses and a lens cover are thermally expanded to cause a positional deviation of the lenses in some cases. In such a case, in the highly-magnified inspection apparatus, an image forming position of the defect varies, and sensitivity to the defect detection becomes unstable. Therefore, temperature maintenance for keeping a constant temperature environment around the inspection apparatus becomes important to make it possible that characteristics of the objective lens are stably secured and the defect is detected with high accuracy.

In general, the inspection apparatus is installed in a clean room, which is controlled in temperature, and under a temperature-controlled environment. However, there are various heat generating sources in the inspection apparatus, and these sources may influence the inspection apparatus to cause fluctuations in temperature. For example, when the table with the mask mounted thereon is moved while a motor is driven, heat is generated from the motor. In addition, heat is also generated from the image sensor at the time of capturing an image. Such generated heat causes the inside of the inspection apparatus to locally increase in temperature, thereby increasing the temperature of the objective lens. Therefore, there is a limitation in the configuration that the inspection apparatus is installed in the clean room to keep the apparatus in a constant temperature from the surrounding area using the temperature maintenance of the clean room, however it is difficult to sufficiently guarantee the temperature of the objective lens.

In light of such a problem, a method is taken into consideration, in which the inspection optical system which includes the light source, the illumination optical system, the objective lens, and the image sensor of the inspection apparatus is housed in a dedicated chamber, and an air conditioner or the like is additionally attached to the chamber to control the temperature inside the chamber. However, even with this method, the local fluctuations in temperature occur in the vicinity of the objective lens as described above, so that the method does not sufficiently solve the problem. In other words, the temperature of the objective lens is not sufficiently guaranteed in the inspection apparatus requiring the high magnification.

The present invention has been made in view of the above problem. In other words, an object of the present invention is to provide an inspection apparatus that stably secures characteristics of the objective lens and detects a defect with high accuracy.

Other challenges and advantages of the present invention are apparent from the following description.

SUMMARY OF THE INVENTION

According to one aspect of the present invention, an inspection apparatus comprising, a light source configured to emit an inspection light, a table configured to mount an inspection target thereon, an illumination optical system configured to direct inspection light from the light source toward the inspection target mounted on the table, an objective lens unit configured to gather transmitting or reflected light generated after the illumination optical system illuminates the inspection target with the inspection light, a light receiving unit configured to capture an optical image formed from the light illuminated through the objective lens unit, a chamber configured to house the table, the light receiving unit, the illumination optical system and the objective lens unit, a temperature adjustment unit configured to adjust a temperature in the chamber, and a gas supply unit configured to be connected to the objective lens unit to supply an inert gas into the objective lens unit from the outside of the chamber, wherein the gas supply unit disposed inside the chamber has a structure in which the temperature of the inert gas supplied into the objective lens unit becomes a predetermined temperature.

Further to this aspect of the present invention, an inspection apparatus, wherein the gas supply unit includes a gas pipe which is bent or curved.

Further to this aspect of the present invention, an inspection apparatus, wherein the bent portion or the curved portion of the gas pipe is provided in a wall of the chamber on a side near the temperature adjustment unit.

Further to this aspect of the present invention, an inspection apparatus, wherein the gas supply unit includes a gas pipe which is longer than a distance between the wall of the chamber and the objective lens unit.

Further to this aspect of the present invention, an inspection apparatus, wherein the objective lens unit includes a plurality of lenses, a plurality of supporting units, each of which supports each of the plurality of lenses, a cover unit which covers the plurality of lenses and the plurality of supporting units, and a flange unit which is provided in an end portion of the cover unit on a side near the light receiving unit, each of the plurality of supporting units and the flange unit are provided with a ventilation hole, the gas supply unit is connected to the ventilation hole of the flange unit, the inert gas is supplied from the ventilation hole of the flange unit to the ventilation hole of at least one of the plurality of supporting units, and the inert gas is further supplied from the ventilation hole to the ventilation hole of another supporting unit.

Further to this aspect of the present invention, an inspection apparatus, wherein the objective lens unit includes a gas flow path which is formed along a sidewall of the cover unit or inside the sidewall of the cover unit, an end portion of the gas flow path on a side near the flange unit is connected to the gas supply unit, and the inert gas supplied from the gas supply unit passes through the gas flow path and is directed toward the table.

In another aspect of the present invention, an inspection apparatus comprising, a light source configured to emit an inspection light, a table configured to mount an inspection target, an illumination optical system configured to direct an inspection light from the light source toward the inspection target mounted on the table, an objective lens unit configured to gather transmitting or reflected light generated after the illumination optical system illuminates the inspection target with the inspection light, a light receiving unit configured to capture an optical image formed from the light illuminated through the objective lens unit, a chamber configured to house the table, the light receiving unit, the illumination optical system and the objective lens unit, a temperature adjustment unit configured to adjust a temperature in the chamber, and a gas supply unit configured to be connected to the objective lens unit to supply an inert gas into the objective lens unit from the outside of the chamber, wherein the gas supply unit disposed inside the chamber includes a gas reservoir which temporarily stores the inert gas supplied into the objective lens unit to make the temperature of the inert gas become a predetermined temperature.

Further to this aspect of the present invention, an inspection apparatus, wherein the objective lens unit includes a plurality of lenses, a plurality of supporting units, each of which supports each of the plurality of lenses, a cover unit which covers the plurality of lenses and the plurality of supporting units, and a flange unit which is provided in an end portion of the cover unit on a side near the light receiving unit, each of the plurality of supporting units and the flange unit are provided with a ventilation hole, the gas supply unit is connected to the ventilation hole of the flange unit, the inert gas is supplied from the ventilation hole of the flange unit to the ventilation hole of at least one of the plurality of supporting units, and the inert gas is further supplied from the ventilation hole to the ventilation hole of another supporting unit.

Further to this aspect of the present invention, an inspection apparatus, wherein the objective lens unit includes a gas flow path which is formed along a sidewall of the cover unit or inside the sidewall of the cover unit, an end portion of the gas flow path on a side near the flange unit is connected to the gas supply unit, and the inert gas supplied from the gas supply unit passes through the gas flow path and is directed toward the table.

DETAILED DESCRIPTION OF THE EMBODIMENTS

Embodiment 1

An inspection apparatus according to the first embodiment of the present invention will be described using the drawings.

Figure 1:
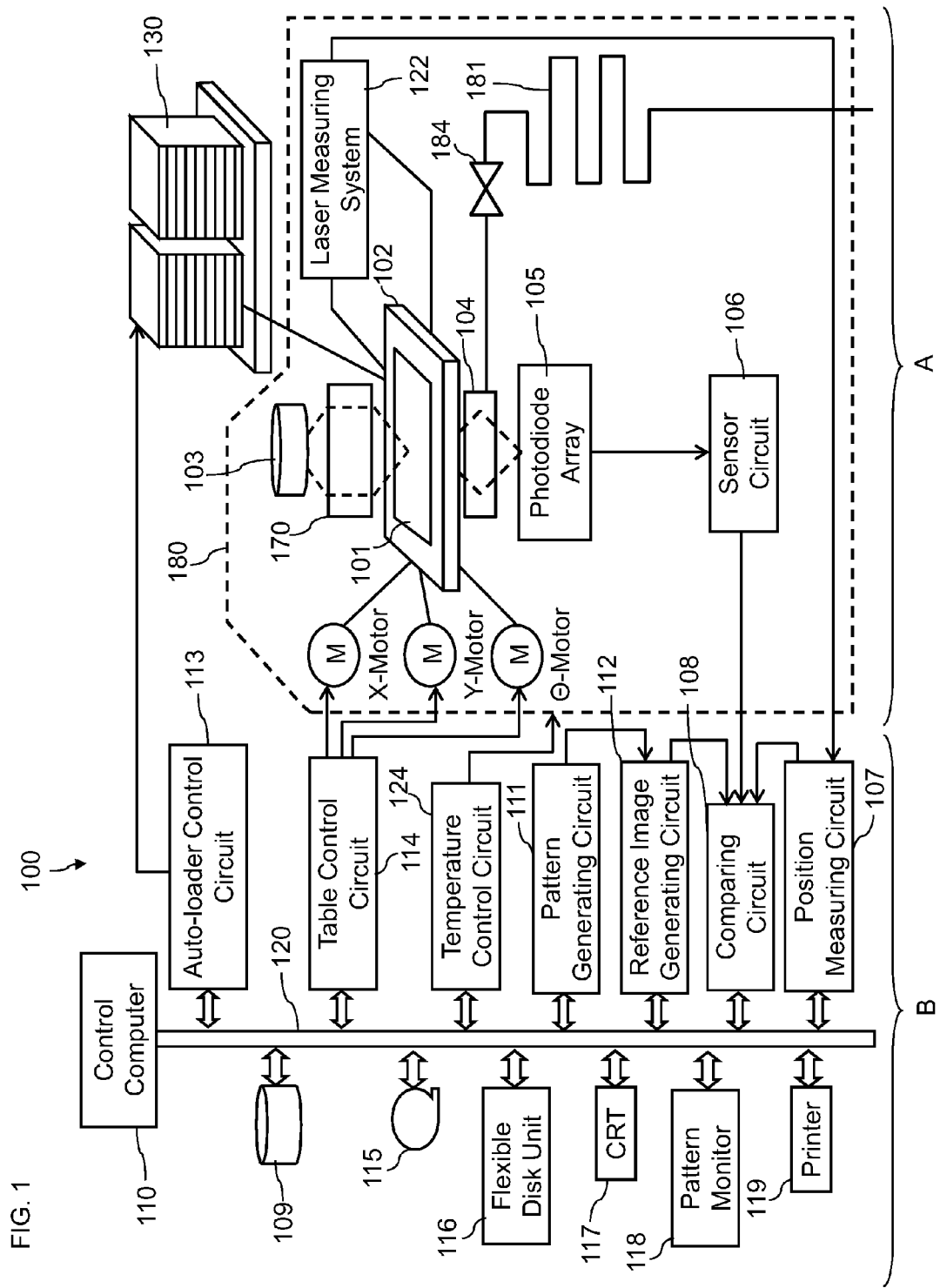
FIG. 1 is a schematic configuration diagram of an inspection apparatus according to a first embodiment.

FIG. 1 is a schematic configuration diagram of an inspection apparatus according to the first embodiment.

In FIG. 1, a configuration unit necessary in the present embodiment is illustrated. However, another well-known configuration unit necessary for an inspection may be used. As used herein, a "unit" or "circuit" can be configured by a program operating on a computer. Alternatively, the "unit" or "circuit" may be constructed by not only the program that is software, but also a combination of software and hardware, or software and firmware. In the case that the "unit" or "circuit" may be constructed by the program, the program can be recorded in a recording device such as a magnetic disk drive.

In the present embodiment, a mask used in photolithography is used as an inspection target. Alternatively, as another example, a wafer may be used as the inspection target.

As illustrated in FIG. 1, an inspection apparatus 100 includes a configuration unit A which acquires an optical image of a mask 101 as an example of the inspection target and a configuration unit B which performs a process necessary for the inspection using the optical image acquired in the configuration unit A. The inspection apparatus 100 further includes a gas pipe 181 as an example of a gas supply unit to supply an inert gas to an objective lens unit 104 which is an example of an objective lens of the configuration unit A in the following description. As illustrated in FIG. 1, the gas pipe 181 may be provided with a flow rate adjustment valve 184 to control a feed rate of the inert gas.

Further, in the present invention, the inert gas refers to a gas having less energy absorption to light which is emitted from a light source 103 of the configuration unit A in the following description, and means a gas having inertness to the light. Specifically, the inert gas in the invention is preferably at least one selected from a group consisting of nitrogen gas, argon gas, and helium gas.

The configuration unit A includes the light source 103 which emits an inspection light, an XYθ-table 102 which is an example of a table for mounting the inspection target mask 101 and movable in the horizontal directions (the X direction and the Y direction) and the rotation direction (the θ direction), an illumination optical system 170 which forms an transmitting illumination system to irradiate the mask 101 mounted on the XYθ-table 102 with the inspection light from the light source 103 in the normal direction (the vertical direction), the objective lens unit 104 which is an example of an objective lens and has lenses disposed in a space defined therein, a photodiode array 105 and a sensor circuit 106 which are an example of a light receiving unit, a laser measuring system 122, and a chamber 180 in which these components are housed. In the chamber 180, there is provided an air conditioner (not illustrated in FIG. 1) as an example of a temperature adjustment unit to adjust the inside of the chamber 180 to a predetermined temperature.

As the light source 103 of the configuration unit A of the inspection apparatus 100, various light sources which emit light having a desired wavelength may be used. For example, a light source which emits a far-ultraviolet light may be used in order to detect a finer defect of the inspection target. In this case, the light emitted from the light source may be absorbed into the air, particularly oxygen, near the objective lens unit 104, inside the inspection apparatus 100, so that the inspection may be hindered. In addition, the oxygen causes a chemical reaction to make the lenses degraded. Therefore, it is desirable that a gas to be supplied to the objective lens unit 104 be selected from the inert gases as described above.

In addition, the configuration unit A may include an auto-loader 130 as illustrated in FIG. 1. Further, the configuration unit B may include an auto-loader control circuit 113 in a case where the configuration unit A includes the automatic loader 130. In the inspection apparatus 100 illustrated in FIG. 1, the light source 103 is disposed inside the chamber 180, but the light source 103 may be disposed outside the chamber.

In the configuration unit A, the optical image of a mask 101 that is an inspection target is acquired. The optical image data of the mask 101 is an image of the mask 101 in which a figure pattern is written based on graphic data included in design pattern data of the mask 101. For example, the optical image data of the mask 101 is 8-bit data with no code, and expresses a gradation of brightness of each pixel.

In the inspection apparatus 100, the mask 101, which is the inspection target, is mounted on the XYθ-table 102 of the configuration unit A. The XYθ-table 102 is moved by an X motor and a Y motor in two horizontal directions, the X and Y directions, orthogonal to each other, and rotated about a vertical θ axis by a θ motor. The laser measuring system 122 measures positions of the XYθ-table 102 in the X direction and the Y direction.

Then, the pattern formed on the mask 101 is illuminated with the inspection light emitted from the light source 103, which is disposed above the XYθ-table 102. More specifically, a light flux emitted from the light source 103 is directed onto the mask 101 through the illumination optical system 170. Under the mask 101, the objective lens unit 104, the photodiode array 105, and the sensor circuit 106 are disposed. The light, which transmits through the mask 101, forms an optical image on the photodiode array 105 through the objective lens unit 104.

The photodiode array 105 performs photoelectric conversion to the pattern image of the mask 101 formed on the photodiode array 105, and the sensor circuit 106 performs A/D (analog-digital) conversion to the pattern image. A plurality of sensor cells (not illustrated) are disposed in the photodiode array 105. A TDI (Time Delay Integration) sensor can be cited as an example of the sensor. In this case, the TDI sensor captures the image of the pattern in the mask 101 while the XYθ-table 102 moves continuously. Further, there is a concern that the photodiode array 105 in use is heated, so that a water cooler is desirably provided for the cooling.

At this point in the configuration unit A, the light source 103, the illumination optical system 170, the object lens unit 104, the photodiode array 105, and the sensor circuit 106 constitute a high-magnification inspection optical system.

The object lens unit 104 of the inspection apparatus 100 according to the present embodiment will be described in detail below.

Figure 2:
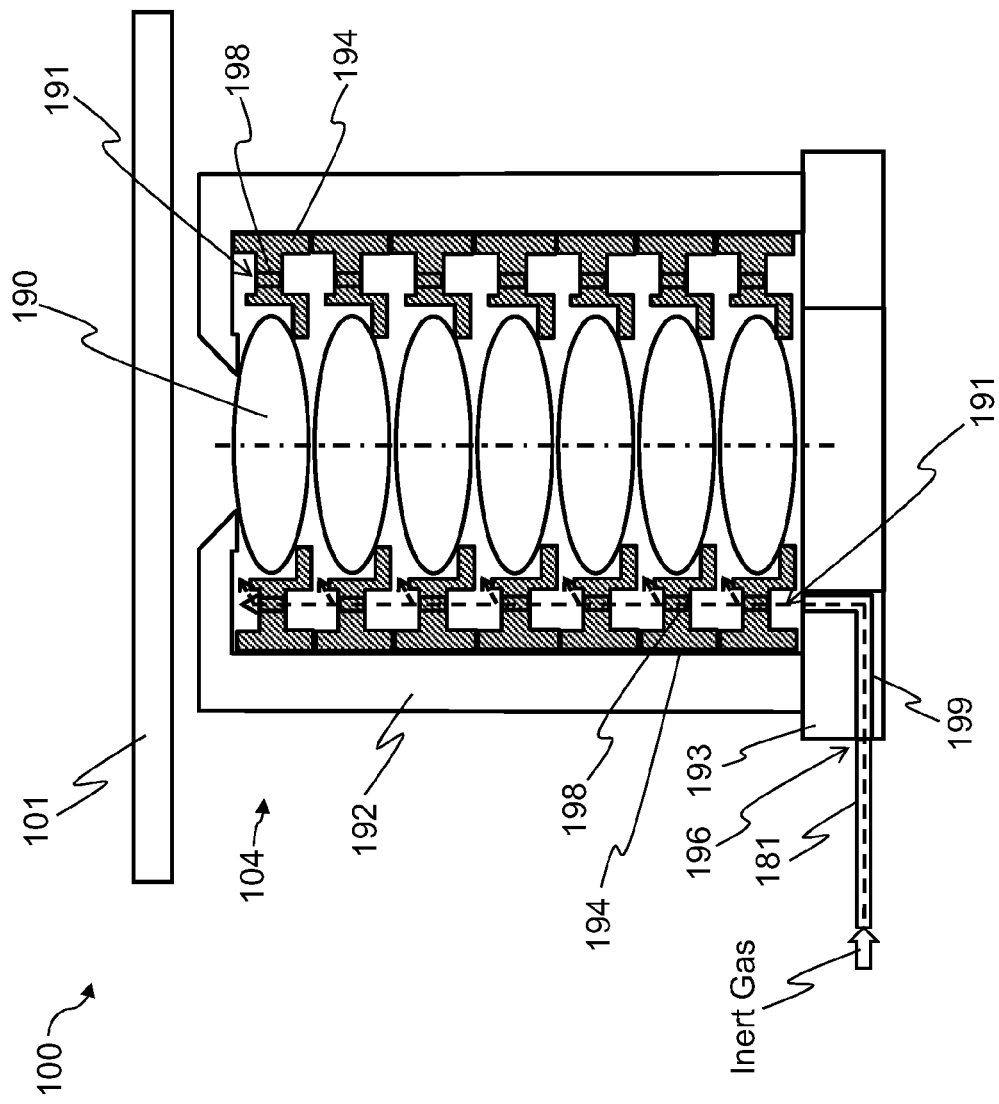
FIG. 2 is a cross-sectional schematic view of the construction of the object lens unit of the inspection apparatus according to the first embodiment of the present invention in FIG. 1.

FIG. 2 is a cross-sectional schematic view of the construction of the object lens unit of the inspection apparatus according to the first embodiment of the present invention.

The objective lens unit 104 is configured to include a lens 190, a lens cell unit 191 which holds the lens 190, a cylindrical lens cover 192 which is an example of a cover unit to cover the lens cell unit 191, and a flange unit 193 which is provided in the end portion of the lens cover 192 on a side near the photodiode array 105 (not illustrated in FIG. 2). The lens 190 is held by a supporting unit, for example, by a holder 194 which is an example of a supporting unit made of a metallic material such as brass in a space partitioned by the lens cell unit 191.

In other words, the objective lens unit 104 has a structure in which the lens cell unit 191 is disposed in the inner space formed by the cylindrical lens cover 192, and the lens 190 is further held in the inner space partitioned by the lens cell unit 191. The flange unit 193 is used to fix the lens cell unit 191 covered by the lens cover 192, the lens 190 disposed therein, and also the lens cover 192 at a predetermined position in the inspection apparatus 100 illustrated in FIG. 1.

Then, the objective lens unit 104 illustrated in FIG. 2 may be configured to include a plurality of lenses 190 arranged in the lens cover 192 from the upper side near the mask 101 toward the lower side near the photodiode array 105 (not illustrated in FIG. 2). In this case, the lens cover 192 of the objective lens unit 104 is configured to include a plurality of lens cell units 191 sequentially arranged therein from the upper side near the mask 101 toward the lower side near the photodiode array 105 to hold the respective lenses 190. In other words, the objective lens unit 104 includes the plurality of lenses 190, a plurality of holders 194 which support the plurality of lenses 190, the lens cover 192 which covers the plurality of lenses 190 and the plurality of holders 194, and the flange unit 193 which is provided in the end portion of the lens cover 192 on a side near the photodiode array 105.

As described above, the inspection apparatus 100 according to the first embodiment of the invention illustrated in FIG. 1 includes the gas pipe 181 as a gas supply unit to supply the inert gas to the objective lens unit 104 of the configuration unit A. Then, as illustrated in FIG. 2, the gas pipe 181 is desirably provided to supply the inert gas to the inside of the objective lens unit 104, that is, the inner space covered by the cylindrical lens cover 192. With this configuration, the inspection apparatus 100 can make the inside of the lens cover 192 into an inert gas atmosphere, and as a result the lens cell units 191 therein can be in an inert gas atmosphere. Then, the inspection apparatus 100 can make the lenses 190 and the holders 194 in the respective lens cell units 191 into an inert gas atmosphere.

The gas pipe 181 and the objective lens unit 104 are desirably connected by, for example, a gas inlet 196 as illustrated in FIG. 2. The flange unit 193 is provided with a ventilation hole 199 which passes therethrough to communicate between the inner space of the objective lens unit 104 and the outer space of the objective lens unit 104. The gas inlet 196 serves as an external port of the ventilation hole 199. Then, the ventilation hole 199 communicates with the inside of the objective lens unit 104, that is, the lens cell units 191, through the internal port. More specifically, the ventilation hole 199 communicates with the inner space of the lens cell units 191 in which the lenses 190 are held.

Therefore, in the inspection apparatus 100, the inert gas supplied from the gas pipe 181 can be supplied into the objective lens unit 104 by connecting the gas pipe 181 to the gas inlet 196 of the flange unit 193.

At this time, the inert gas passes into the flange unit 193 through the gas inlet 196, and is supplied into the lens cell unit 191 at the lowest portion of the objective lens unit 104. In the objective lens unit 104 of the inspection apparatus 100 according to the present embodiment, the lens cell units 191 serve to partition the inner space to hold the lenses 190. For this reason, in a case where the objective lens unit 104 includes the plurality of lens cell units 191 arranged therein, ventilation holes 198 are formed in the respective holders 194 to make the inner spaces of the adjacent lens cell units 191 communicate with each other. Therefore, by supplying the inert gas to the lens cell unit 191 at the lowest portion of the objective lens unit 104, the inert gas can be sequentially supplied even in the lens cell units 191 disposed in the upper portion through the ventilation holes 198. In other words, by connecting the gas pipe 181 to the ventilation hole of the flange unit 193, the inert gas is supplied from the ventilation hole 199 of the flange unit 193 to one ventilation hole 198 disposed at the lowest portion among the plurality of holders 194, and the inert gas is further supplied from the ventilation hole 198 where the inert gas has been supplied to the ventilation hole 198 of another holder 194.

Then, in the objective lens unit 104, the inert gas is finally discharged from the lens cell unit 191 at the uppermost portion toward the mask 101 disposed thereupon. As a result, all the lens cell units 191 included in the objective lens unit 104 can be put in an inert gas atmosphere, and all the lenses 190 and the holders 194 held thereon can be put in the flow of the inert gas.

The inspection apparatus 100 having such structures of the objective lens unit 104 and the gas pipe 181 can put the lenses 190 and the holders 194 in the objective lens unit 104 into the inert gas atmosphere using the inert gas supplied from the gas pipe 181. Then, the lenses 190 and the holders 194 in the objective lens unit 104 can be put in the flow of the inert gas.

Therefore, in a case where a temperature-controlled inert gas can be used as the inert gas supplied from the gas pipe 181, the objective lens unit 104 can be directly controlled in temperature using the inert gas. In other words, by supplying an inert gas controlled at a desired temperature from the gas pipe 181 into the objective lens unit 104, the temperature of the objective lens unit 104 can be set to the desired temperature more effectively.

As a result, in the inspection apparatus 100, the lenses 190 and the holders 194 configured in the objective lens unit 104 can be controlled at the desired temperature. Therefore, in the inspection apparatus 100, the objective lens unit 104 can be maintained in temperature at the desired temperature by supplying the inert gas from the gas pipe 181, thereby guaranteeing the temperature.

The inspection apparatus 100 according to the present embodiment further includes a mechanism that controls the inert gas supplied from the gas pipe 181 at the desired temperature.

As described above, for example, the inspection apparatus as in the embodiment is typically disposed in a clean room when used. In this case, the inside of the clean room is maintained within a temperature range suitable for the inspection apparatus. However, in a case where the inert gas is supplied to the inspection apparatus in the clean room, the inert gas is supplied from the outside of the clean room through the gas pipe. Usually in this case, that the temperature of the inert gas is not maintained.

Therefore, for example, even when the temperature-unmaintained inert gas is supplied into the objective lens unit 104 of the inspection apparatus 100 according to the present embodiment while using the inert gas as it is, it is difficult to realize maintenance at the desired temperature. For this reason, the inspection apparatus 100 according to the present embodiment realizes a temperature control on the inert gas using the gas pipe 181.

As described above, the inspection apparatus 100 illustrated in FIG. 1 includes the light source 103, the XYθ-table 102, the illumination optical system 170, the objective lens unit 104, the photodiode array 105, the sensor circuit 106, the laser measuring system 122, and the like, all of which are housed in the chamber 180. Then, the inspection apparatus 100 can maintain the temperature inside the chamber 180 using a temperature adjustment unit, for example, a dedicated air conditioner. In other words, the inspection apparatus 100 maintains the inside of the chamber 180 to be at the desired temperature. As a result, the inspection apparatus 100 is configured to maintain the temperature of components such as the objective lens unit 104 against the surrounding environment.

Therefore, the inspection apparatus 100 according to the present embodiment is configured to make a temperature control on the inert gas supplied into the objective lens unit 104 using the temperature maintenance in the chamber 180 and using the gas pipe 181. As a result, even in a case where local fluctuations in temperature occur in the vicinity of the objective lens unit 104, the objective lens unit 104 can be correspondingly controlled in temperature at the desired constant temperature.

Furthermore, in a case where the inspection apparatus 100 is installed under a temperature-maintained environment such as in the clean room, the temperature maintenance can also be used for the temperature control on the inert gas performed using the gas pipe 181.

Figure 3:
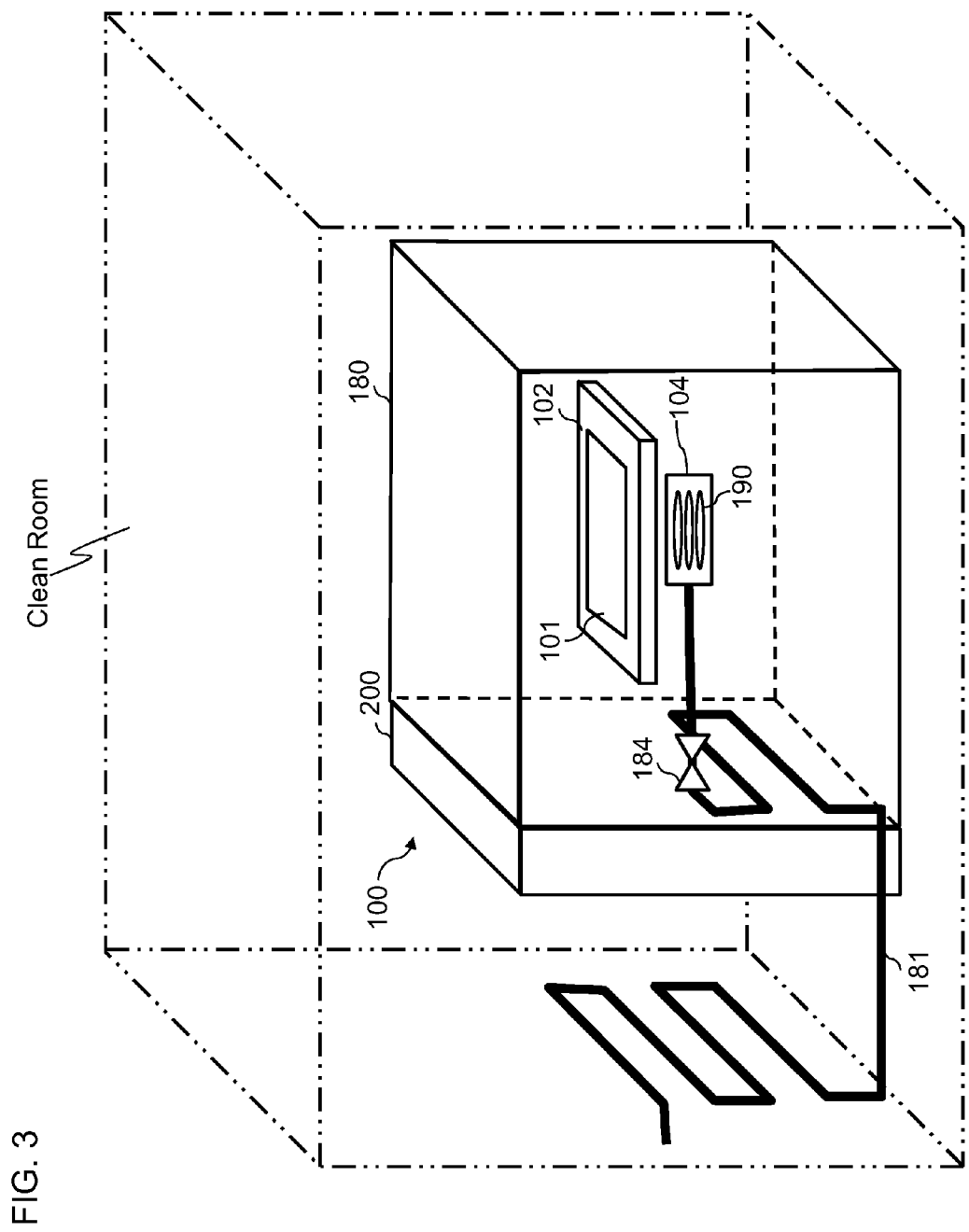
FIG. 3 is a diagram schematically illustrating an inspection apparatus according to the first embodiment of the invention, which is installed in the clean room.

FIG. 3 is a diagram schematically illustrating an inspection apparatus according to the first embodiment of the invention, which is installed in the clean room.

FIG. 3 schematically illustrates, the chamber 180 which is a main component of the inspection apparatus 100 according to the present embodiment, the air conditioner 200 which is an example of the temperature adjustment unit additionally attached to the chamber 180 to adjust the inside of the chamber 180 at a predetermined temperature, the gas pipe 181, the objective lens unit 104 in which the lens 190 is held, the XYθ-table 102 on which the mask 101 is mounted, and the like.

The inspection apparatus 100 according to the present embodiment, for example, is desirably installed and used in the clean room of which the temperature is maintained. In a typical clean room, for example, the facilities of gas pipes are provided to supply the inert gas such as nitrogen gas to the apparatuses installed in the clean room. The inspection apparatus 100 according to the present embodiment supplies the inert gas to the objective lens unit 104, and in this case the inert gas such as nitrogen gas prepared as a facility in the typical clean room can be used as the inert gas. In other words, the gas pipe 181 of the inspection apparatus 100 may be connected between the gas pipe (not illustrated) included in the clean room and the objective lens unit 104 of the inspection apparatus 100 so as to supply the inert gas such as nitrogen gas to the objective lens unit 104.

Usually, at this time, the inert gas such as nitrogen gas supplied from the facilities of gas pipes installed in the clean room is not maintained in temperature. For this reason, as described above, the prepared inert gas is not suitable for the use as it is, but needs to be controlled in temperature. In the inspection apparatus 100 according to the present embodiment, the length and arrangement structure of the gas pipe 181 are optimized and the temperature maintenance in the chamber 180 is used, so that the temperature control on the inert gas is realized through the gas pipe 181.

The gas pipe 181 of the inspection apparatus 100 according to the present embodiment is connected to the inert gas pipe (not illustrated) installed in the clean room, and connected to the gas inlet 196 (not illustrated in FIG. 3) of the objective lens unit 104 provided in the chamber 180 through the wall of the chamber 180 from the wall portion of the clean room outside the chamber 180. In other words, the inspection apparatus 100 includes the gas pipe 181 which is connected to the objective lens unit 104 such that the inert gas for temperature control is supplied into the objective lens unit 104 from the outside of the chamber 180. In the gas pipe 181, the flow rate adjustment valve 184 may be provided to control the feed rate of the inert gas.

Then, the inside of the chamber 180 becomes a space of which the temperature is adjusted to be a desired preset temperature by the air conditioner 200. Therefore, the inspection apparatus 100 uses the chamber 180 of which the temperature is set. Then, the portion of the gas pipe 181 disposed in the chamber 180 is made to have a sufficient length for making the temperature of the inert gas supplied into the objective lens unit 104 through the pipe become the preset temperature of the chamber 180. In other words, the inert gas supplied from the outside of the chamber 180 toward the objective lens unit 104 is adjusted in its flow rate by the flow rate adjustment valve 184, and the temperature of the inert gas becomes the preset temperature of the chamber 180, that is, the desired preset temperature of the objective lens unit 104 while the gas passes through the gas pipe 181.

Therefore, the gas pipe 181 which can make such a temperature control on the inert gas has bent portions or curved portions in the chamber 180 as illustrated in FIG. 3. Then, the gas pipe 181 is provided to be longer than the distance between the wall of the chamber 180 and the objective lens unit 104. At this time, in a case where the inert gas is supplied at a desired flow rate from the gas pipe 181 to the objective lens unit 104, it is desirable that the length of the portion of the gas pipe 181 disposed in the chamber 180 become a sufficient length for making the temperature of the gas become the preset temperature of the chamber 180.

In addition, it is desirable that the portion of the gas pipe 181 disposed in the chamber 180 have an arrangement structure suitable for making the temperature of the inert gas, which is supplied into the objective lens unit 104 through the portion, become the preset temperature of the chamber 180.

As illustrated in FIG. 3, the air conditioner 200 is provided in a sidewall portion of the chamber 180 of the inspection apparatus 100 to make a temperature control on the inside of the chamber 180. In the inspection apparatus 100, a part of the portion of the gas pipe 181 disposed in the chamber 180 is disposed on the sidewall where the air conditioner 200 of the chamber 180 is installed. For example, the bent portions or the curved portions of the gas pipe 181 are disposed on a sidewall portion of the air conditioner 200. Then, the inert gas passing into the gas pipe 181 is efficiently controlled in temperature by the air conditioner 200. In addition, since there is a concern that the photodiode array 105 is heated, it is desirable that the gas pipe 181 be disposed at a position as far away from the photodiode array 105 as possible.

In addition, in the inspection apparatus 100 according to the present embodiment, the temperature maintenance performed in the clean room can also be used for the temperature control, which is performed on the inert gas through the gas pipe 181. As illustrated in FIG. 3, the portion of the gas pipe 181 disposed outside the chamber 180 in the clean room is made to have a sufficient length for making the temperature of the inert gas supplied into the objective lens unit 104 through the portion become the preset temperature of the chamber 180 in the clean room.

Therefore, as illustrated in FIG. 3, the portion of the gas pipe 181 disposed outside the chamber 180 includes the bent portions or the curved portions, and is longer than the distance between the wall of the clean room and the wall of the chamber 180. At this time, in a case where the inert gas is supplied at a desired flow rate from the gas pipe 181 to the objective lens unit 104, it is desirable that the length of the portion of the gas pipe 181 disposed in the chamber 180 become a sufficient length for making the temperature of the gas become the preset temperature of the clean room. In addition, the gas pipe 181 may have a circular cross-sectional structure of its portion disposed in the clean room, and otherwise, for example, a flat elliptical shape or the like may be selectively employed to increase a contact area with the inert gas.

With the structure of the gas pipe 181 described above, the inspection apparatus 100 according to the present embodiment can make the temperature control on the inert gas supplied into the objective lens unit 104 using the temperature maintenance in the chamber 180 and using the gas pipe 181. As a result, even in a case where local fluctuations in temperature occur in the vicinity of the objective lens unit 104 due to an image sensor (not illustrated in FIG. 3) and the like, the objective lens unit 104 can be controlled in temperature at the desired constant temperature while excluding the influence.

Then, it is possible to stably secure the characteristics of the objective lens unit 104 so that a high-resolution optical image is acquired in the photodiode array 105 and the sensor circuit 106. Further, it is possible to detect defects with a high accuracy.

In addition, in the inspection apparatus 100 according to the present embodiment, the temperature maintenance can be realized by supplying the temperature-controlled inert gas to the objective lens unit 104 using the gas pipe 181 as illustrated in FIG. 2. However, the temperature-maintained inert gas may be used for other purposes. In other words, it is possible to configure the apparatus to use the temperature-controlled inert gas passing through the gas pipe 181 such that the lens surface of the objective lens unit 104 on a side near the mask 101 is purged by the inert gas.

Figure 4:
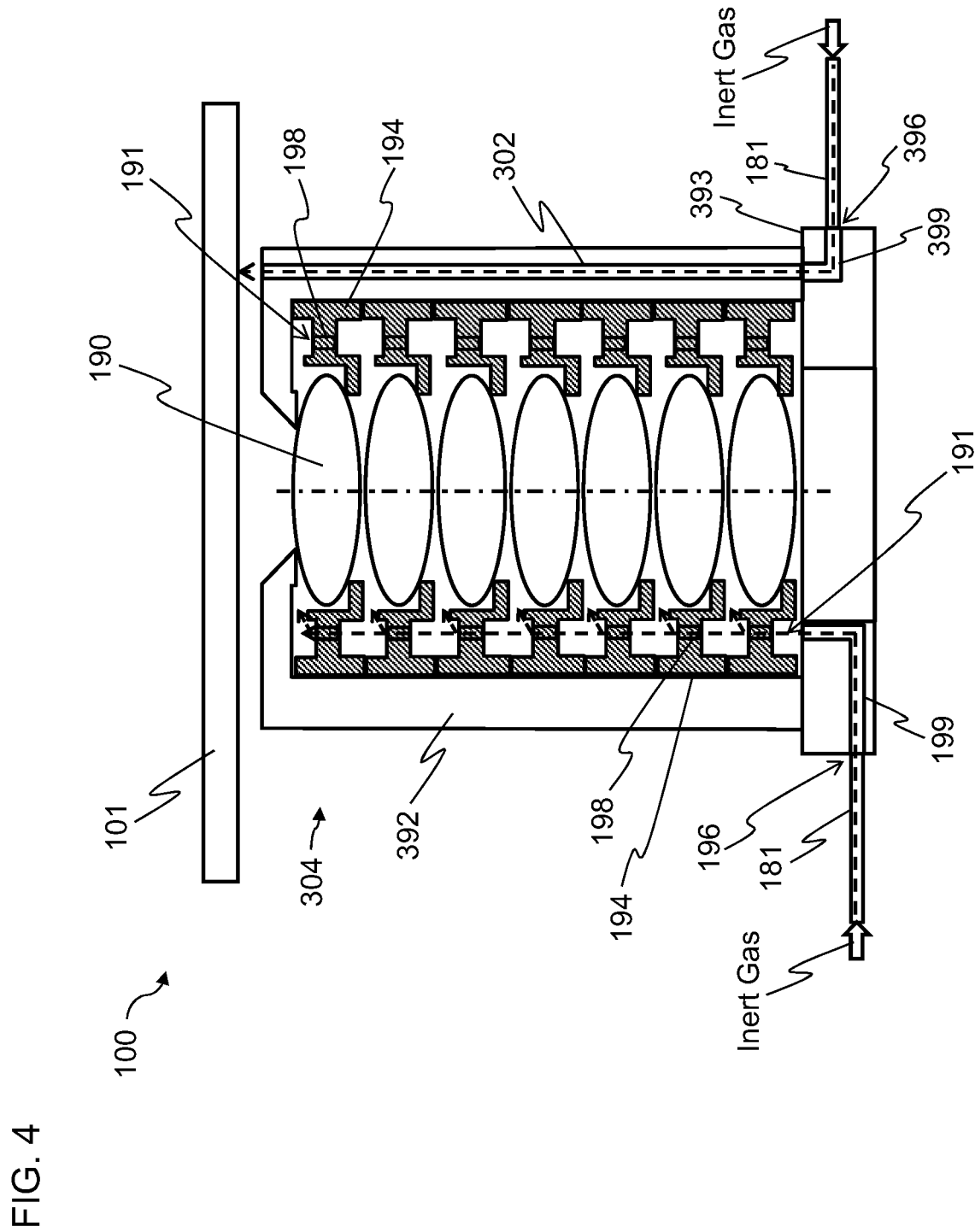
FIG. 4 is a cross-sectional view schematically illustrating the structure of the objective lens unit, which is another example of the inspection apparatus according to the first embodiment of the invention.

FIG. 4 is a cross-sectional view schematically illustrating the structure of the objective lens unit, which is another example of the inspection apparatus according to the first embodiment of the invention.

An objective lens unit 304, which is another example of the inspection apparatus according to the first embodiment of the invention, is provided with a flow path 302 inside the sidewall of a cylindrical lens cover 392 in order to make the inert gas flow. The flow path 302 is formed to be extended from an end portion of the lens cover 392 on a side near a photodiode array 105 (not illustrated in FIG. 4) of a flange unit 393 to an end portion on a side near the XYθ-table 102 (not illustrated in FIG. 4) on which the mask 101 is mounted. Then, the flange unit 393 is provided with a ventilation hole 399 that passes through the flange unit and communicates with the flow path 302.

The objective lens unit 304 has the same structure as that of the above-mentioned objective lens unit 104 of FIG. 2 except that the flow path 302 is provided inside the sidewall of the lens cover 392 and the ventilation hole 399 is provided in the flange unit 393. Therefore, the common components will be denoted by the same reference numerals, and the redundant descriptions will not be repeated.

In the objective lens unit 304, the ventilation hole 399 of the flange unit 393 includes a gas inlet 396 that is an external port and serves as an inlet of the inert gas. Then, as described above, the end terminal on the other side of the ventilation hole 399 is connected to the end portion of the flow path 302 provided in the lens cover 392. Then, the flow path 302 of the lens cover 392 passes into the sidewall of the lens cover 392, and the end terminal portion on the other side is extended up to the lens surface of the lens cover 392 on a side near the mask 101 and opened to form an outlet of the inert gas.

Therefore, in the objective lens unit 304, the gas pipe 181 branches off in the middle of the pipe and one of the branch pipes is connected to the gas inlet 196 while the other one is connected to the gas inlet 396, so that the temperature-controlled inert gas can be supplied to the ventilation hole 399. Then, the inert gas supplied to the ventilation hole 399 passes through the flow path 302 of the lens cover 392 connected to the ventilation hole 399, and is directed toward the XYθ-table 102 from the end portion of the objective lens unit 304 on a side near the XYθ-table 102 on which the mask 101 is mounted.

As a result, the objective lens unit 304 can purge the lens surface of the objective lens unit 304 on a side near the mask 101 with the inert gas. Then, even when the mask 101 is moved while being mounted on the XYθ-table 102, a space between the mask 101 and the objective lens unit 104 can be put in an inert gas atmosphere.

In addition, the inert gas supplied from the gas inlet 396 passes through the ventilation hole 399 of the flange unit 393 and the flow path 302 of the lens cover 392. Therefore, the objective lens unit 304 can also make the temperature control on the lens cover 392 and the flange unit 393 using the temperature-maintained inert gas.

Further, the objective lens unit 304 of FIG. 4 is illustrated to have one flow path 302 in the sidewall of the lens cover 392, but the number of flow paths 302 is not limited to one. For example, another flow path can be provided inside the sidewall portion (the sidewall portion on the left side in FIG. 4) at a position facing the flow path 302 with the lens 190 interposed therebetween. Furthermore, still another flow path can be provided inside the sidewall of the lens cover 392 at a position separated from the other paths. In the plurality of flow paths thus provided, the inert gas pipe which branches off from the gas pipe 181 is connected to the flow path 302 of FIG. 4 in the same manner, and the temperature-controlled inert gas is supplied.

The objective lens unit 304 thus structured as above, which is another example of the inspection apparatus according to the first embodiment of the invention, can be maintained in temperature and purge the lens surface with the inert gas. Therefore, it is possible to stably acquire the high-resolution optical image in the configuration unit A. Further, it is possible for the inspection apparatus 100 to inspect the defect with a high accuracy.

In addition, in the objective lens unit 304 as illustrated in FIG. 4, the flow path 302 of the lens cover 392 is formed inside the sidewall, but the path can also be provided using an appropriate pipe disposed on the sidewall of the lens cover 392 along the lens cover 392. In this case, it is desirable that an end portion of the pipe serving as the flow path of the inert gas be disposed on the outer side of the flange unit 393 while also not providing the ventilation hole 399 in the flange unit 393. Then, the gas pipe 181 branches off in the middle of the pipe and one of the branch pipes is connected to the end portion of the pipe on a side near the flange unit 393, so that the temperature-controlled inert gas can be supplied into the pipe. The inert gas supplied into the pipe flows along the sidewall of the lens cover 392 through the pipe. Thereafter, the inert gas is directed toward the XYθ-table 102 from the end portion of the objective lens unit 304 on a side near the XYθ-table 102 on which the mask 101 is mounted.

As a result, the objective lens unit 304 using the pipe as the flow path of the inert gas can purge the lens surface of the objective lens unit 304 on a side near the mask 101 with the inert gas. Then, even when the mask 101 is moved while being mounted on the XYθ-table 102, a space between the mask 101 and the objective lens unit 304 can be put in an inert gas atmosphere.

Next, the configuration unit B of the inspection apparatus 100 will be described in which processes necessary for the inspection are performed using the optical image acquired in the configuration unit A described above.

As shown in FIG. 1, in the configuration unit B, the control computer 110, that is, the controller controlling the whole of the inspection apparatus 100 is connected to a temperature control circuit 124 which controls the temperature of the chamber 180 of the configuration unit A, a position measuring circuit 107, a comparing circuit 108, a reference image generating circuit 112, an pattern generating circuit 111, an auto-loader control circuit 113, a table control circuit 114, a magnetic disk drive 109 that is an example of the storage device, a magnetic tape device 115, a flexible disk drive 116, a CRT (Cathode Ray Tube) 117, a pattern monitor 118, and a printer 119 through a bus 120 that constitutes a data transmission line.

As described above, the "unit" or "circuit" in FIG. 1 can be configured as a program operating on the computer. Alternatively, the "unit" or "circuit" may be constructed by not only the program, that is software, but also a combination of software and hardware, or software and firmware. In the case that the "unit" or "circuit" may be constructed by the program, the program can be recorded in the magnetic disk drive 109. For example, each of the temperature control circuit 124, the auto-loader control circuit 113, the table control circuit 114, the comparing circuit 108, and the position measuring circuit 107 may be constructed by an electric circuit, the software that can be processed by the control computer 110, or the combination of the electric circuit and the software.

The control computer 110 controls the temperature control circuit 124 to control the temperature of the chamber 80 of the configuration unit A.

The control computer 110 controls the table control circuit 114 to drive the XYθ-table 102. A moving position of the XYθ-table 102 is measured by the laser measuring system 122, and transmitted to the position measuring circuit 107.

The design pattern data that becomes reference data of the die-to-database method is stored in the magnetic disk drive 109. In the progress of the inspection, the design pattern data is read and transmitted to the pattern generating circuit 111. In the pattern generating circuit 111, the design pattern data is converted into image data (design image data). After that, this image data is sent to the reference image generating circuit 112 to generate a reference image data.

In the comparing circuit 108, the optical image data which is sent from the sensor circuit 106, and the reference image data which is generated in the reference image generating circuit 112, are compared to each other using a proper comparison determination algorithm. As a result of the comparison, in the case that a difference between the two exceeds a predetermined threshold, the position is determined to be the defect.

Further, the inspection apparatus 100 according to the present embodiment may include other well-known elements, which are necessary for inspecting the mask 101 in addition to the components illustrated in FIG. 1. For example, the inspection apparatus itself may include a review tool to be described below.

Figure 5:
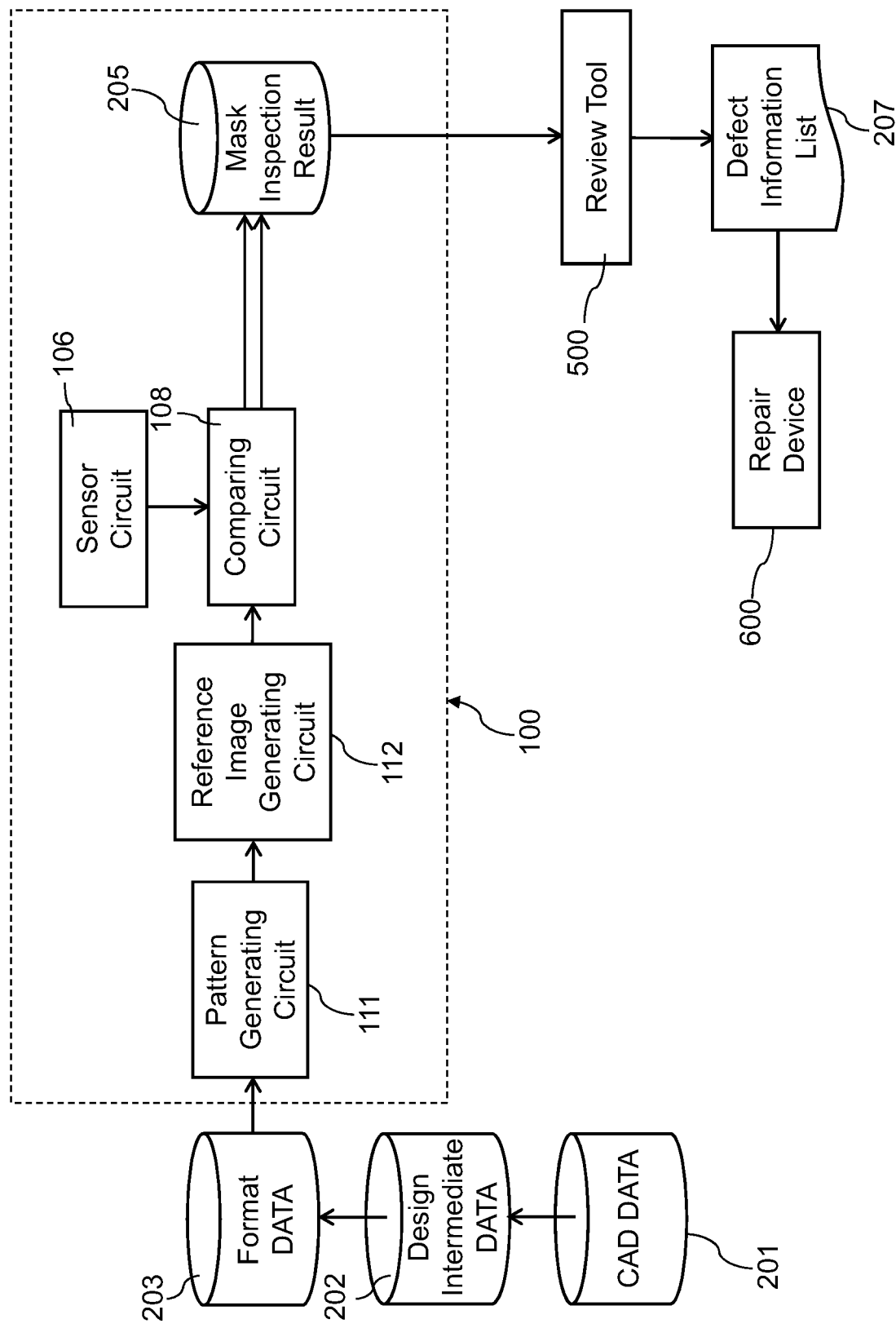
FIG. 5 is a view illustrating a data flow according to the first embodiment of the present invention.

FIG. 5 is a view illustrating a data flow according to the first embodiment of the present invention.

As illustrated in FIG. 5, CAD data 201 produced by a designer (user) is converted into design intermediate data 202 having a hierarchical format. The pattern data, which is produced in each layer and formed in the mask 101, is stored in the design intermediate data 202. At this point, generally the inspection apparatus is configured not to directly read design intermediate data 202. That is, independent format data is used by each manufacturer of an inspection apparatus. For this reason, the design intermediate data 202 is input to the inspection apparatus 100 after conversion into format data 203 unique to the inspection apparatus in each layer. In this case, the format data 203 can be set to a data format that is unique to the inspection apparatus 100.

Next, an example of a method for inspecting the mask 101 with the inspection apparatus 100 in FIG. 1 will be described below. Through the description of an inspection method according to the present embodiment in which the inspection apparatus 100 is used, the functions of the respective elements of the configuration unit A and the configuration unit B will be described in more detail.

Figure 6:
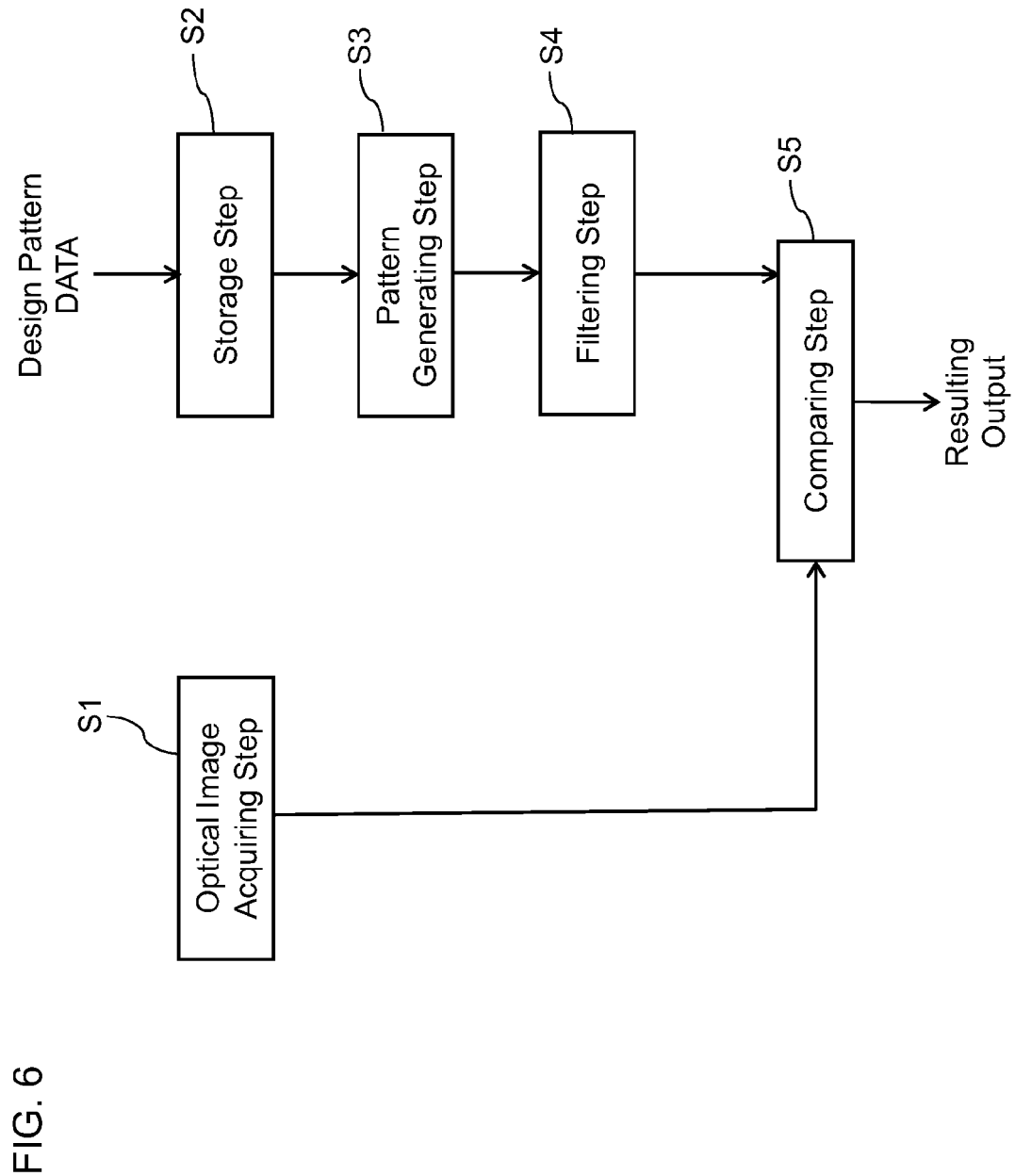
FIG. 6 is a flowchart illustrating the inspection method.

FIG. 6 is a flowchart illustrating the inspection method.

The inspection method by die-to-database comparison method will be described below. Therefore, a reference image data which is compared with an optical image data of the sample to be inspected is a reference image data which is generated based on a design data (design pattern data). In the present embodiment, an inspection apparatus can be adopted to the inspection method by the die-to-die comparison method. In this case, the reference image data becomes the optical image data different from the optical image data of the inspection target.

As shown in FIG. 6, the inspection process includes an optical image acquiring step (S1), a storage step for design pattern data (S2), a pattern generating step (S3), a filtering step (S4), a comparing step between an optical image data and a reference image data (S5).

<Acquiring Step>

In the optical image acquiring step (S1) as shown in FIG. 6, the configuration unit A (of FIG. 1) acquires an optical image data (a measurement data) of the mask 101. The optical image data is the image data of the mask 101 on which pattern figures are written based on pattern figure data included in the design pattern. One example of a process in which an optical image data is acquired will be described using FIGS. 1 and 6.

The mask 101 is mounted on the XYθ-table 102. The XYθ-table 102 is moved in the X direction and the Y direction, which are two horizontal directions orthogonal to each other, respectively, and is rotated about the vertical θ axis. The XYθ-table 102 can be moved in the X and Y directions and rotated in a θ direction by a drive system such as a 3-axis (X-Y-θ) motor driven by the table control circuit 114 under the control of the control computer 110 as shown in FIG. 1. These X-, Y-, and θ-axis motors may be, for example, step motors. The laser measuring system 122 measures the moving position of the XYθ-table 102, and the measurement data is sent to the position measuring circuit 107. In the case that the inspection apparatus 100 includes the auto loader 130, the mask 101 on the XYθ-table 102 is automatically loaded from the auto loader 130 driven by the auto-loader control circuit 113, and upon completion of the inspection, the mask 101 is automatically retrieved from the XYθ-table 102.j The light source 103 emits the inspection light onto the mask 101 that is the inspection target. The light output from the light source 103 transmits through the illumination optical system 170 and is focused on the mask 101. The illumination optical system 170, for example, is configured to include lenses such as a condenser lens and mirrors.

As illustrated in FIG. 1, the light, which is emitted from the light source 103 and transmits through the mask 101 forms an optical image on the photodiode array 105 through the objective lens unit 104.

At this time, as described with the use of FIGS. 2 and 3, the objective lens unit 104 is connected to the gas pipe 181 to supply the temperature-controlled inert gas around the lens 190 and the holder 194 in the objective lens unit 104. The temperature control of the inert gas is realized such that the control computer 110 causes the temperature control circuit 124 to control the temperature of the chamber 180 of the configuration unit A.

In other words, the inert gas supplied into the objective lens unit 104 is controlled in temperature by using the temperature maintenance of the chamber 180 for the temperature control of the inert gas and further using the gas pipe 181. In other words, the gas pipe 181 is configured such that the portion of the gas pipe 181 disposed in the temperature-maintained chamber 180 has a sufficient length, and the inert gas at the same temperature as the maintained temperature of the chamber 180 is controlled by the flow rate adjustment valve 184 and supplied into the objective lens unit 104.

As a result, even in a case where local fluctuations in temperature occur in the vicinity of the objective lens unit 104 due to the image sensor (not illustrated in FIG. 3) and the like, the objective lens unit 104 can be controlled in temperature (thermal uniformization) to be a desired constant temperature while excluding the influence. Then, with the use of the objective lens unit 104 of which the temperature is guaranteed with high accuracy, the optical image can be stably formed in the photodiode array 105, and sensitivity to the defect detection can be stabilized.

The pattern image formed on the photodiode array 105 as shown in FIG. 1 is photoelectrically converted by the photodiode array 105 and A/D (analog to digital) converted by the sensor circuit 106 into an optical image data. An image sensor is arranged in the photodiode array 105. As for the image sensor according to the present embodiment, for example, a line sensor composed of CCD (charge coupled devices) cameras lined up serving as an imaging device can be used. The line sensor may be, for example, TDI (Time Delay Integration) sensors. Thus, the pattern in the mask 101 is imaged by these TDI sensors while the XYθ-table 102 is continuously moved in the positive or negative X direction.

The optical image data, which was acquired in the optical image acquiring step (S1), is sent to the comparing circuit 108 as shown in FIG. 1 and FIG. 6.

<Storage Step>

In FIG. 6, S2 is the storage step. In FIG. 1, the design pattern data that was used to form the pattern in the mask 101 is stored in the magnetic disk unit 109 serving as a storage unit.

The designed pattern includes graphic pattern figures each consisting of basic pattern figures such as rectangles and triangles. The magnetic disk unit 109 stores feature data indicating the shape, size, and position of each pattern feature, specifically, information such as the coordinates (x, y) of the reference position of each feature, the length of its sides, and a shape code (or identifier) identifying the type of shape, such as a rectangle or triangle.

A set of graphic patterns existing within a range of several tens of micrometers is generally called a cluster or a cell, and the data is layered using the cluster or cell. In the cluster or cell, a disposition coordinate and a repetitive amount are defined in the case that various graphic patterns are separately disposed or repetitively disposed with a certain distance. The cluster or cell data is disposed in a strip-shaped region called a stripe. The strip-shaped region has a width of several hundred micrometers and a length of about 100 mm that corresponds to a total length in an X-direction or a Y-direction of the mask 101.

<Pattern Generating Step>

At the pattern generating step (S3) in FIG. 6, the pattern generating circuit 111 reads design pattern data of the mask 101 from the magnetic disk unit 109 through the control computer 110 and converts it into 2-bit or other multiple-bit image data (design image data). This image data is sent to the reference image generating circuit 112.

After the design pattern data to be the feature data was input to the pattern generating circuit 111, the pattern generating circuit 111 generates data of each pattern feature, and interprets the shape code in the data indicative of the shape of the pattern feature and obtains its dimensions. The pattern generating circuit 111 then divides the pattern into a virtual grid of squares (or grid elements) having predetermined quantization dimensions, and generates 2-bit or other multiple-bit design image data of the design pattern segment in each grid element. By using the generated design image data, the pattern generating circuit 111 calculates the design pattern occupancy in each grid element (corresponding to a sensor pixel). This pattern occupancy in each pixel represents the pixel value.

<Filtering Step>

At the filtering step (S4) in FIG. 6, the design image data as an image data of the feature sent by the reference image generating circuit 112 (of FIG. 1) is performed appropriate filtering.

Figure 7:
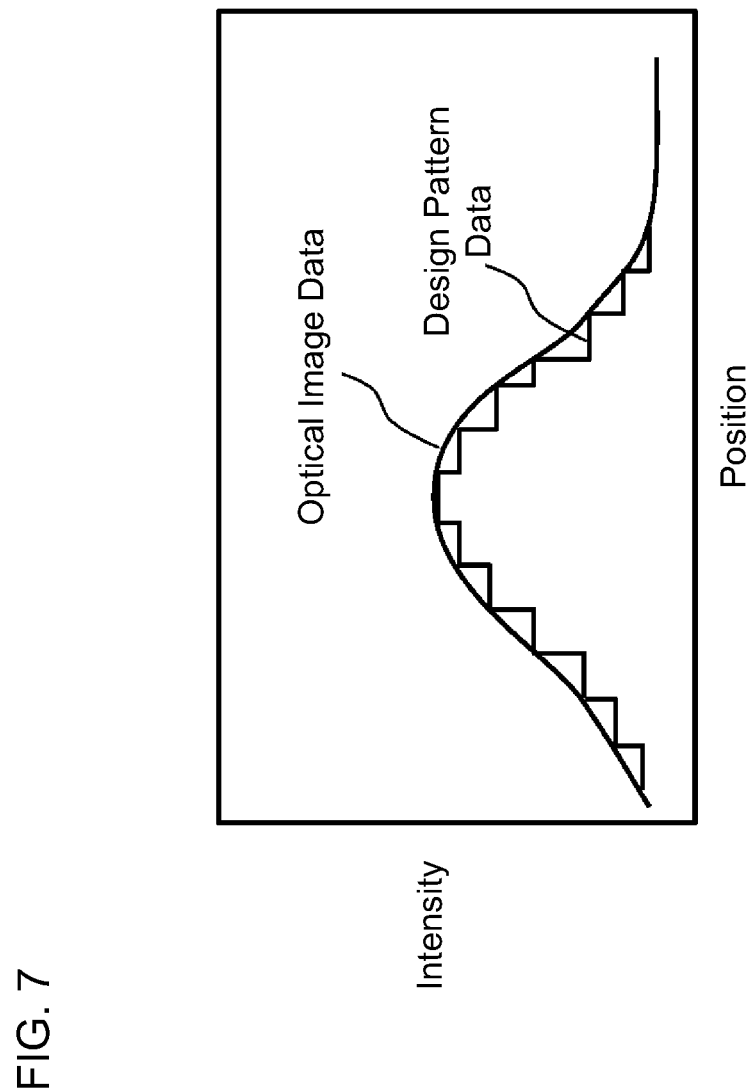
FIG. 7 shows the filtering step.

FIG. 7 shows the filtering step.

The measurement data as an optical image data output from the sensor circuit 106 as shown in FIG. 1 is somewhat "blurred" due to the resolution characteristics of the object lens unit 104 and due to the aperture effect in the photodiode array 105, that is, this optical image is a spatially low-pass filtered image. Therefore, since the design image data corresponding to the optical image is digital data consisting of digital values representing the intensity (or gray scale) of each point of the image, this design image data may be filtered to match the "blurred" optical image, or measurement data. In this way, a reference image data to be compared with the optical image data is produced.

<Comparing Step>

S5 as shown in FIG. 6 is the comparing step. As shown in FIG. 1, the optical image is sent from the sensor circuit 106 to the comparing circuit 108. The design pattern data is converted into reference image data by the pattern generating circuit 111 and the reference image generating circuit 112, and then is sent to the comparing circuit 108. The position data output from the position measuring circuit 107 which connects to the laser measuring system 122 and detects the position on the mask 101 of the optical image, is input to the comparing circuit 108.

The comparing circuit 108 compares each portion of the optical image data received from the sensor circuit 106 with the corresponding portion of the reference image data generated by the reference image generating circuit 112 in accordance with a suitable comparison determination algorithm, and if the difference between these portions exceeds a predetermined value, the comparing circuit 108 determines that the portion of the optical image data is defective. Then the coordinates of that portion, the optical image data, and the reference image data, on which the detection of the defect is based, are stored as a mask inspection result 205 (see FIG. 5) in the magnetic disk unit 109.

Identification of defects can be performed according to the following two types of methods. One method is directed to identifying defects when there is a difference exceeding a predetermined threshold dimension between a position of the outline of the reference image and a position of the outline of the optical image. The other method is directed to identifying defects when the ratio of the line width of the pattern in the reference image and the line width of the pattern in the optical image exceeds a predetermined threshold. With the latter method, the ratio of the distance between patterns in the reference image and the distance between patterns in the optical image may be used for identification of defects.

The mask inspection result 205 is transmitted to a review tool 500 as illustrated in FIG. 5. A review process is an operation in which the operator determines whether the detected defect will become a practical problem. Specifically, the mask inspection result 205 is sent to a review tool 500, the review is performed by the operator who determines whether the defect found in the inspection can be tolerated. The operator can compare and review the reference image as a basis for the defect judgment with the optical image, which includes the defect.

In the review tool 500, an image of the mask 101 in a defect portion is displayed while moving the table on which the mask 101 is mounted to observe the coordinates of the defects one by one. In addition, the determination condition of the defect and the optical image and reference image used as grounds for the determination are displayed side by side on the screen of the computer provided in the review tool 500 in order to make verification at the same time.

Further, in a case where the review tool 500 is provided in the inspection apparatus 100, the image of the mask 101 in the defect portion is displayed using an optical system of the inspection apparatus 100. In addition, the determination condition of the defect and the optical image and reference image used as grounds for the determination are simultaneously displayed using the screen of the control computer 110 illustrated in FIG. 1.

The information of a defect determined through the review process is stored in the magnetic disk unit 109 as shown in FIG. 1. When even one defect to be repaired is confirmed in the review tool 500, the mask 101 is sent, with a defect information list 207, to a repair device 600, which is an external device of the inspection apparatus 100. Since the repair method is different according to the type of defect, that is, between the extrusion and intrusion defects, the type of the defect, including determination between the extrusion and intrusion defects and the coordinates of the defect are added to the defect information list 207.

Embodiment 2

An inspection apparatus according to the second embodiment of the present invention will be described using the drawings below.

The inspection apparatus according to the second embodiment of the invention includes the configuration unit A in which the optical image is acquired, similar to the configuration unit A of the above-mentioned inspection apparatus 100 according to the first embodiment, and the configuration unit B in which the processes necessary for the inspection are performed using the optical image acquired in the configuration unit A, similar to the configuration unit B of the above-mentioned inspection apparatus 100 according to the first embodiment. Further, a gas pipe is included as an example of the gas supply unit, which supplies the inert gas to the objective lens unit of the configuration unit A. The inspection apparatus according to the second embodiment has the same structure as the above-mentioned inspection apparatus 100 according to the first embodiment except that the structure of the gas pipe is different. Therefore, the inspection method using the inspection apparatus according to the second embodiment is also the same as the inspection method performed by the above-mentioned inspection apparatus 100 according to the first embodiment.

Therefore, in the following description of the inspection apparatus according to the second embodiment of the invention, the common components with the inspection apparatus 100 according to the first embodiment will be denoted by the same reference numerals, and the redundant descriptions will not be repeated. Then, the description will be made mainly on the gas pipe having a different structure from the first embodiment and the objective lens unit to which the inert gas is supplied using the gas pipe.

Figure 8:
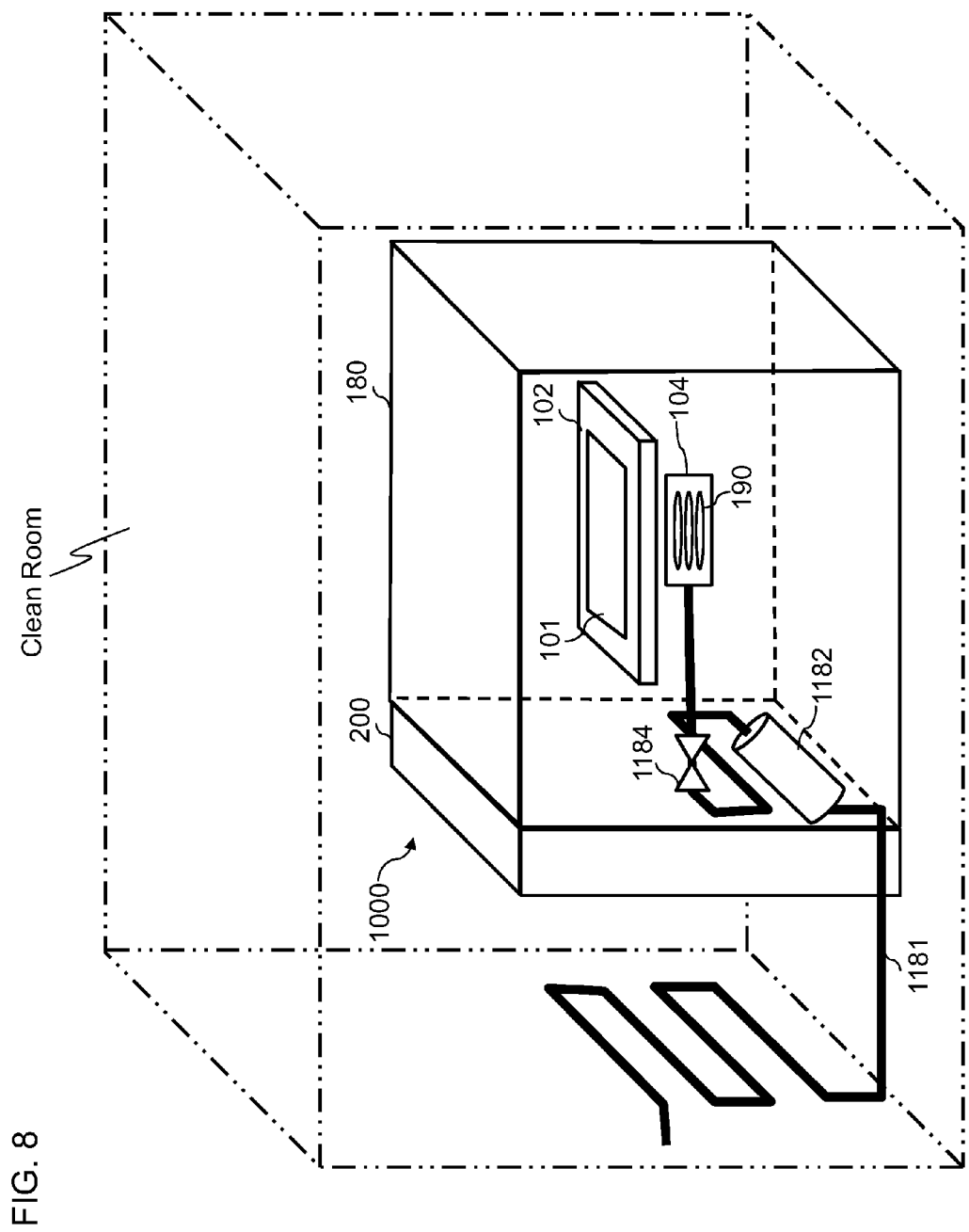
FIG. 8 is a diagram schematically illustrating an inspection apparatus according to the second embodiment of the invention, which is installed in the clean room.

FIG. 8 is a diagram schematically illustrating an inspection apparatus according to the second embodiment of the invention, which is installed in the clean room.

The configuration unit A of an inspection apparatus 1000 according to the present embodiment includes the light source 103 (not illustrated) which emits the inspection light, the XYθ-table 102 (not illustrated) which is movable in the horizontal directions (the X direction, the Y direction) and the rotation direction (the θ direction), the illumination optical system 170 (not illustrated) which forms an transmitting illumination system to irradiate the mask 101 mounted on the XYθ-table with the inspection light from the light source 103 in the normal direction (the vertical direction), the objective lens unit 104 (not illustrated) which has the lenses disposed in the space defined therein, the photodiode array 105 (not illustrated) and the sensor circuit 106 (not illustrated) which are an example of a light receiving unit, the laser measuring system 122 (not illustrated), and the chamber 180 in which these components are housed.

In FIG. 8, similarly to FIG. 3, the chamber 180 of the inspection apparatus 1000 according to the present embodiment, the air conditioner 200 which is additionally attached to the chamber 180 to adjust the inside of the chamber 180 at a predetermined temperature, a gas pipe 1181 which is an example of the gas supply unit, the objective lens unit 104, the XYθ-table 102 on which the mask 101 is mounted, and the like are schematically illustrated for the sake of convenience. In the gas pipe 1181, a flow rate adjustment valve 1184 is provided similarly to the flow rate adjustment valve 184 of the gas pipe 181 of the above-mentioned inspection apparatus 100 according to the first embodiment. In addition, a gas tank 1182 as an example of a gas reservoir is provided in the middle of the gas pipe 1181 as to be described below.

The inspection apparatus 1000 according to the present embodiment, for example, is desirably installed and used in the clean room of which the temperature is maintained. In a typical clean room, for example, the facilities of gas pipes are provided to supply the inert gas such as nitrogen gas to the apparatuses installed in the clean room. The inspection apparatus 1000 according to the present embodiment supplies the inert gas to the objective lens unit 104, and in this case the inert gas such as nitrogen gas which is prepared in a facility in the typical clean room can be used as the inert gas. In other words, the gas pipe 1181 of the inspection apparatus 1000 is connected to the gas pipe (not illustrated) included in the clean room so as to supply the inert gas such as nitrogen gas to the objective lens unit 104.

Usually, at this time, the inert gas such as nitrogen gas supplied from the facilities of gas pipes installed in the clean room is not maintained in temperature as described above. For this reason, also in the inspection apparatus 1000, the prepared inert gas is not suitable for the use as it is, but needed to be controlled in temperature.

The inspection apparatus 1000 according to the present embodiment includes the gas tank 1182, as an example of the gas reservoir, which temporarily stores the inert gas, in a portion of the gas pipe 1181 disposed in the chamber 180. Then, the inert gas supplied from the outside of the chamber 180 into the gas tank 1182 is temporarily stored to make the temperature of the inert gas become a preset temperature of the chamber 180 using the temperature maintenance in the chamber 180. As a result, the inspection apparatus 1000 realizes the temperature control on the inert gas using the gas pipe 1181.

More specifically, on the one hand, the gas pipe 1181 of the inspection apparatus 1000 according to the present embodiment is connected to the inert gas pipe (not illustrated) included in the clean room. Then, on the other hand, the gas pipe 1181 is connected to the gas inlet 196 (not illustrated in FIG. 8) of the objective lens unit 104 provided in the chamber 180 through the wall of the chamber 180 from the wall portion of the clean room outside the chamber 180. In other words, the inspection apparatus 1000 includes the gas pipe 1181 connected to the objective lens unit 104 to supply the inert gas for the temperature control from the outside of the chamber 180 into the objective lens unit 104. The gas pipe 1181 includes the gas tank 1182 inside the chamber 180 to temporarily store the inert gas. In addition, the flow rate adjustment valve 1184 may be provided in the gas pipe 1181 to control the feed rate of the inert gas.

The inside of the chamber 180 becomes a space of which the temperature is adjusted to be a preset temperature by the air conditioner 200. The inspection apparatus 1000 can supply the temperature-controlled inert gas into the objective lens unit 104 using the temperature-set chamber 180 and the above-mentioned gas tank 1182.

In other words, the inert gas supplied from the pipe of the clean room to the gas pipe 1181 is temporarily stored in the gas tank, which is provided in a portion of the gas pipe 1181 disposed in the chamber 180 to make the temperature of the inert gas become the preset temperature in the chamber 180. Then, after the temperature is adjusted, the inert gas is adjusted in its flow rate by the flow rate adjustment valve 1184, and supplied to the objective lens unit 104 for the temperature control of the objective lens unit 104.

Therefore, in a case where the inert gas is supplied at a desired flow rate from the gas pipe 1181 to the objective lens unit 104, it is desirable that the gas tank 1182 included in the gas pipe 1181 have a sufficient volume for making the temperature of the gas reach the preset temperature of the chamber 180.

In addition, it is desirable that the portion of the gas pipe 1181 disposed in the chamber 180 have an arrangement structure suitable for making the temperature of the inert gas, which is supplied into the objective lens unit 104 through the portion, become the preset temperature of the chamber 180.

As illustrated in FIG. 8, the air conditioner 200 is provided in a sidewall of the chamber 180 of the inspection apparatus 1000 to adjust the inside of the chamber 180 to a predetermined temperature. In the inspection apparatus 1000, a part of the portion of the gas pipe 1181 disposed in the chamber 180 is disposed on the sidewall where the air conditioner 200 of the chamber 180 is installed. Then, the gas tank 1182 included in the gas pipe 1181 is disposed on a sidewall of the air conditioner 200. As a result, the inert gas temporarily stored in the gas tank 1182 is efficiently controlled in temperature by the air conditioner 200. In addition, since there is a concern that the photodiode array 105 (not illustrated) is heated, it is desirable that the gas pipe 1181 be disposed at a position as far away from the photodiode array 105 as possible.

In addition, similarly to the above-mentioned inspection apparatus 100 of FIG. 3 according to the first embodiment, the temperature maintenance performed in the clean room can also be used in the inspection apparatus 1000 according to the present embodiment, and the gas pipe 1181 can be used for the temperature control on the inert gas.

As illustrated in FIG. 8, the portion of the gas pipe 1181 disposed outside the chamber 180 in the clean room is made to have a sufficient length for making the temperature of the inert gas supplied into the objective lens unit 104 through the portion become the preset temperature of the chamber 180 in the clean room.

Therefore, as illustrated in FIG. 8, the portion of the gas pipe 1181 disposed outside the chamber 180 includes the bent portions or the curved portions, and is longer than the distance between the wall of the clean room and the wall of the chamber 180. At this time, in a case where the inert gas is supplied at a desired flow rate from the gas pipe 1181 to the objective lens unit 104, it is desirable that the length of the portion of the gas pipe 1181 disposed in the chamber 180 become a sufficient length for making the temperature of the gas become the preset temperature of the clean room.

With the structure of the gas pipe 1181 described above, the inspection apparatus 1000 according to the present embodiment can make the temperature control on the inert gas supplied into the objective lens unit 104 using the temperature maintenance in the chamber 180 and using the gas pipe 1181 and the gas tank 1182. As a result, even in a case where local fluctuations in temperature occur in the vicinity of the objective lens unit 104 due to an image sensor (not illustrated in FIG. 8) and the like, the objective lens unit 104 can be controlled in temperature at the desired constant temperature while excluding the influence.

As a result, it is possible to stably secure the characteristics of the objective lens unit 104 so that a high-resolution optical image is acquired in the photodiode array 105 and the sensor circuit 106. Further, it is possible to detect defects with a high accuracy.

In addition, in the inspection apparatus 1000 according to the present embodiment, the temperature maintenance of the objective lens unit 104 can be realized by supplying the temperature-controlled inert gas to the objective lens unit 104 using the gas pipe 1181. At this time, similarly to the inspection apparatus 100 according to the first embodiment, the temperature-adjusted inert gas may be used for other purposes. In other words, the objective lens unit 304 illustrated in FIG. 4 can be used as the objective lens unit. Then, it is possible to configure the inspection apparatus 1000 to use the temperature-controlled inert gas passing through the gas pipe 1181 such that the lens surface of the objective lens unit 304 on a side near the mask 101 is purged by the inert gas.

Further, a method of inspecting the mask 101 using the inspection apparatus 1000 illustrated in FIG. 8 can be performed in the same manner as the above-mentioned method of inspecting the mask 101 using the inspection apparatus 100 illustrated in FIG. 1. In other words, the inspection method can be performed according to the same die-to-database method as described above.

In this case, in the optical image acquisition process, the control is performed by the flow rate adjustment valve 1184 of the gas pipe 1181, and it is desirable that the inert gas be not introduced into the objective lens unit 104 until the inert gas stored in the gas tank 1182 is at a predetermined temperature. In other words, after the temperature of the inert gas is adjusted in the gas tank 1182 to be a desired preset temperature of the chamber 180, the inert gas is supplied to the objective lens unit 104. Then, the objective lens unit 104 comes into a state of being at a preset temperature by the supply of the inert gas. With the use of the objective lens unit 104 of which the temperature is guaranteed with a high accuracy, the inspection apparatus 1000 can make an optical image in the photodiode array 105 formed stably, and make the sensitivity to the defect detection stabilized.

The present invention is not limited to the embodiments described and can be implemented in various ways without departing from the spirit of the invention.

The above description of the present embodiment has not specified apparatus constructions, control methods, etc. which are not essential to the description of the invention, since any suitable apparatus constructions, control methods, etc. can be employed to implement the invention. Further, the scope of this invention encompasses all inspection methods and apparatuses employing the elements of the invention and variations thereof, which can be designed by those skilled in the art.

What is claimed is:

1. An inspection apparatus comprising:
   a light source configured to emit an inspection light;
   a table configured to mount an inspection target thereon;
   an illumination optical system configured to direct the inspection light from the light source toward the inspection target mounted on the table;
   an objective lens unit configured to gather transmitting or reflected light generated after the illumination optical system illuminates the inspection target with the inspection light;
   a light receiving unit configured to capture an optical image formed from the light illuminated through the objective lens unit;
   a chamber configured to house the table, the illumination optical system, the objective lens unit and the light receiving unit;
   a temperature adjustment unit configured to adjust a temperature in the chamber; and a gas supply unit configured to be connected to the objective lens unit to supply an inert gas into the objective lens unit from the outside of the chamber, wherein the gas supply unit disposed inside the chamber has a structure in which the temperature of the inert gas supplied into the objective lens unit becomes a predetermined temperature.

2. The inspection apparatus according to claim 1, wherein the gas supply unit includes a gas pipe which is bent or curved.

3. The inspection apparatus according to claim 2, wherein the bent portion or the curved portion of the gas pipe is provided in a wall of the chamber on a side near the temperature adjustment unit.

4. The inspection apparatus according to claim 1, wherein the gas supply unit includes a gas pipe which is longer than a distance between the wall of the chamber and the objective lens unit.

5. The inspection apparatus according to claim 1, wherein the objective lens unit includes a plurality of lenses, a plurality of supporting units, each of which supports each of the plurality of lenses, a cover unit which covers the plurality of lenses and the plurality of supporting units, and a flange unit which is provided in an end portion of the cover unit on a side near the light receiving unit, each of the plurality of supporting units and the flange unit are provided with a ventilation hole, the gas supply unit is connected to the ventilation hole of the flange unit, the inert gas is supplied from the ventilation hole of the flange unit to the ventilation hole of at least one of the plurality of supporting units, and the inert gas is further supplied from the ventilation hole to the ventilation hole of another supporting unit.

6. The inspection apparatus according to claim 5, wherein the objective lens unit includes a gas flow path which is formed along a sidewall of the cover unit or inside the sidewall of the cover unit, an end portion of the gas flow path on a side near the flange unit is connected to the gas supply unit, and the inert gas supplied from the gas supply unit passes through the gas flow path and is directed toward the table.

7. An inspection apparatus comprising:

a light source configured to emit an inspection light;

a table configured to mount an inspection target;

an illumination optical system configured to direct the inspection light from the light source toward the inspection target mounted on the table;

an objective lens unit configured to gather transmitting or reflected light generated after the illumination optical system illuminates the inspection target with the inspection light;

a light receiving unit configured to capture an optical image formed from the light illuminated through the objective lens unit;

a chamber configured to house the table, the light receiving unit, the illumination optical system and the objective lens unit;

a temperature adjustment unit configured to adjust a temperature in the chamber; and a gas supply unit configured to be connected to the objective lens unit to supply an inert gas into the objective lens unit from the outside of the chamber, wherein the gas supply unit disposed inside the chamber includes a gas reservoir which temporarily stores the inert gas supplied into the objective lens unit to make the temperature of the inert gas become a predetermined temperature.

8. The inspection apparatus according to claim 7, wherein the objective lens unit includes a plurality of lenses, a plurality of supporting units, each of which supports each of the plurality of lenses, a cover unit which covers the plurality of lenses and the plurality of supporting units, and a flange unit which is provided in an end portion of the cover unit on a side near the light receiving unit, each of the plurality of supporting units and the flange unit are provided with a ventilation hole, the gas supply unit is connected to the ventilation hole of the flange unit, the inert gas is supplied from the ventilation hole of the flange unit to the ventilation hole of at least one of the plurality of supporting units, and the inert gas is further supplied from the ventilation hole to the ventilation hole of another supporting unit.

9. The inspection apparatus according to claim 8, wherein the objective lens unit includes a gas flow path which is formed along a sidewall of the cover unit or inside the sidewall of the cover unit, an end portion of the gas flow path on a side near the flange unit is connected to the gas supply unit, and the inert gas supplied from the gas supply unit passes through the gas flow path and is directed toward the table.

* * * * *